US012657715B2

(12) United States Patent (10) Patent No.: US 12,657,715 B2
Jia et al. (45) Date of Patent: Jun. 16, 2026

(54) METHODS AND DEVICES FOR MEDICAL IMAGE PROCESSING

(71) Applicant: SHANGHAI UNITED IMAGING HEALTHCARE CO., LTD., Shanghai (CN)

(72) Inventors: Feng-Gang Jia, Shanghai (CN); Wen-Jun Yu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 401 days.

(21) Appl. No.: 18/141,412

(22) Filed: Apr. 29, 2023

(65) Prior Publication Data

US 2023/0351597 A1 Nov. 2, 2023

(30) Foreign Application Priority Data

Apr. 29, 2022 (CN) .......................... 202210465291.6

(51) Int. Cl.
*G06T 7/00* (2017.01)
*G06T 5/50* (2006.01)
(Continued)

(52) U.S. Cl.
CPC .............. *G06T 7/0014* (2013.01); *G06T 5/50* (2013.01); *G06T 7/11* (2017.01); *G06T 7/194* (2017.01);
(Continued)

(58) Field of Classification Search
CPC ......... G16H 30/40; G06T 5/50; G06T 7/0014; G06T 7/11; G06T 7/194; G06T 7/246;
(Continued)

(56) References Cited

U.S. PATENT DOCUMENTS

| | | | | |
|---|---|---|---|---|
| 2005/0265611 | A1* | 12/2005 | Valadez | ................... G06T 7/32 382/236 |
| 2014/0003690 | A1* | 1/2014 | Razeto | ................... A61B 6/507 382/131 |
| 2015/0161789 | A1* | 6/2015 | Roujol | ................... G06F 18/22 382/131 |

FOREIGN PATENT DOCUMENTS

| | | |
|---|---|---|
| CN | 1973311 A | 5/2007 |
| CN | 102646164 A | 8/2012 |

(Continued)

OTHER PUBLICATIONS

Loktyushin et al. "Blind retrospective motion correction of MR images." Magnetic resonance in medicine 70.6 (2013): 1608-1618. (Year: 2013).*

(Continued)

*Primary Examiner* — Katrina R Fujita

(57) ABSTRACT

A method for medical image processing is disclosed. The method includes: acquiring a plurality of frames of medical image data including a reference frame and at least one floating frame, each of the reference frame and the floating frame including a target region and a background region; performing image segmentation on the reference frame to obtain a mask for the target region in the reference frame; performing, based on the reference frame and the mask, motion correction on the floating frame to obtain a motion corrected image corresponding to the floating frame, and performing motion analysis on the target region in the motion corrected image. A computer apparatus and a non-volatile computer readable storage medium for medical image processing are also disclosed.

18 Claims, 9 Drawing Sheets

(51) Int. Cl.
    *G06T 7/11*        (2017.01)
    *G06T 7/194*     (2017.01)
    *G16H 30/40*    (2018.01)

(52) U.S. Cl.
    CPC ... *G16H 30/40* (2018.01); *G06T 2207/30048*
                        (2013.01)

(58) Field of Classification Search
    CPC ............. G06T 7/33; G06T 2207/20201; G06T
                            2207/30048
    See application file for complete search history.

(56) References Cited

FOREIGN PATENT DOCUMENTS

| | | | |
|---|---|---|---|
| CN | 108022261 | A | 5/2018 |
| CN | 110310314 | A | 10/2019 |
| CN | 111062963 | A | 4/2020 |
| CN | 113393498 | A | 9/2021 |
| CN | 113628293 | A | 11/2021 |
| CN | 113676655 | A | 11/2021 |
| CN | 114255265 | A | 3/2022 |

OTHER PUBLICATIONS

Schmidt-Richberg et al. "A flexible variational registration framework." Insight Journal (2014). (Year: 2014).*
Werner et al. "Estimation of lung motion fields in 4D CT data by variational non-linear intensity-based registration: A comparison and evaluation study." Physics in Medicine & Biology 59.15 (2014): 4247. (Year: 2014).*
Office Action (CN Application No. 202210465291.6), dated Nov. 28, 2024, 7 pages.

* cited by examiner

Magnetic Resonance
Scanning Apparatus

Computer Apparatus

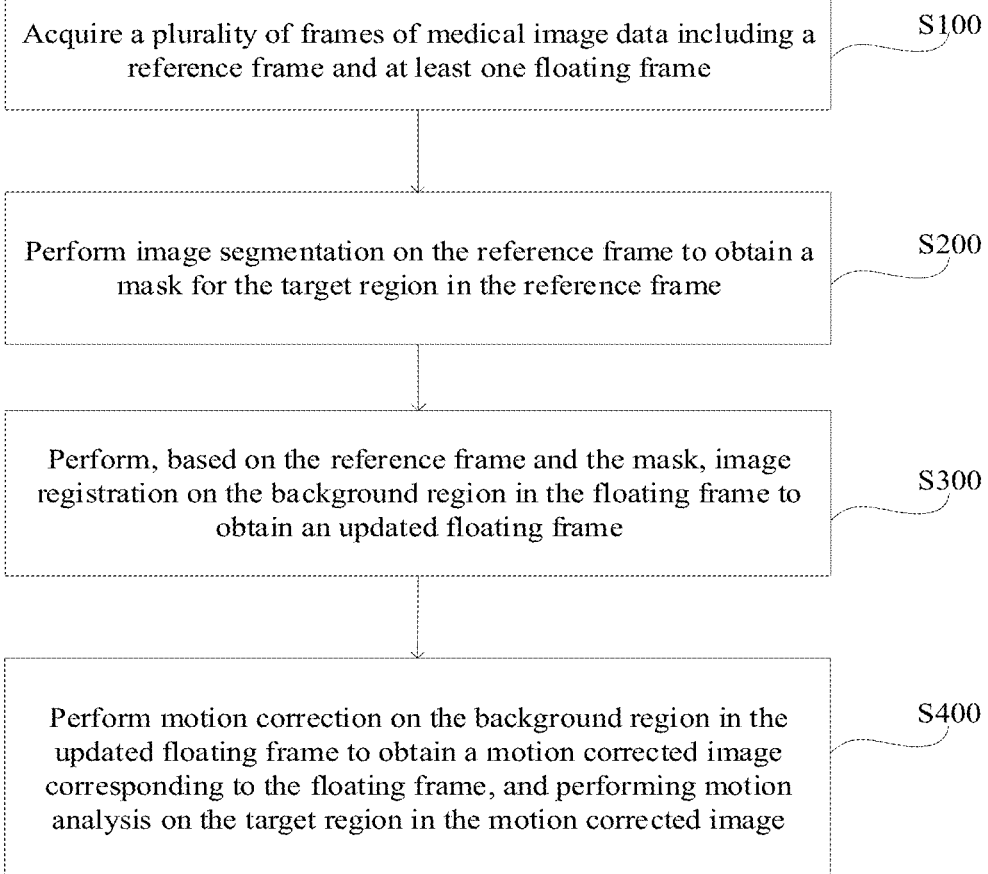

Acquire a plurality of frames of medical image data including a reference frame and at least one floating frame — S100

Perform image segmentation on the reference frame to obtain a mask for the target region in the reference frame — S200

Perform, based on the reference frame and the mask, image registration on the background region in the floating frame to obtain an updated floating frame — S300

Perform motion correction on the background region in the updated floating frame to obtain a motion corrected image corresponding to the floating frame, and performing motion analysis on the target region in the motion corrected image — S400

FIG. 2

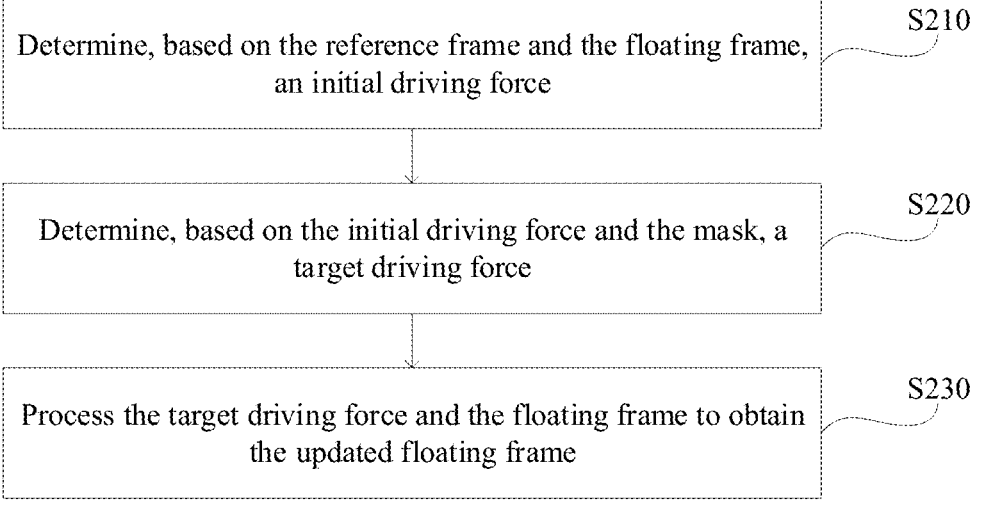

Determine, based on the reference frame and the floating frame, an initial driving force — S210

Determine, based on the initial driving force and the mask, a target driving force — S220

Process the target driving force and the floating frame to obtain the updated floating frame — S230

FIG. 3

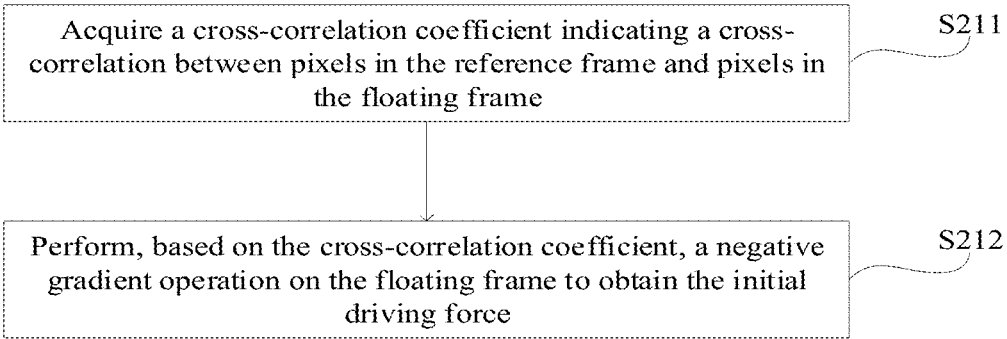

Acquire a cross-correlation coefficient indicating a cross-correlation between pixels in the reference frame and pixels in the floating frame — S211

Perform, based on the cross-correlation coefficient, a negative gradient operation on the floating frame to obtain the initial driving force — S212

FIG. 4

Diaphragm Region
Boundary Line

Diaphragm Region
Boundary Offset
Line

Diaphragm Region
Boundary Line

METHODS AND DEVICES FOR MEDICAL IMAGE PROCESSING

CROSS REFERENCE TO RELATED APPLICATION

The present application claims priority to Chinese patent application No. 202210465291.6, filed on Apr. 29, 2022. The content of the above identified Chinese patent application is hereby incorporated in its entirety by reference.

TECHNICAL FIELD

The present disclosure relates to the technology field of medical technology, and more particularly, to a method for medical image processing, and a computer apparatus and a non-volatile computer readable storage medium for the same.

BACKGROUND

In clinical practice, the role of time dimensions in cinematograph images is to evaluate the motion of certain organs, but human organ motions include heart motions, respiratory motions, intestinal peristalsis, etc., and multiple organ motions are coupled together. Therefore, in order to analyze the motion of a target organ and avoid affecting the respiratory motion of other organs, it is necessary to correct the respiratory motion of other organs to protect the respiratory motion of the target organ.

In conventional art, the respiratory motion of other organs is corrected using a motion model of rotation, translation, miscut, time or space angle to protect the respiratory motion of other organs. However, in a conventional manner, there is a problem in that the respiratory motion correction image is inaccurate.

SUMMARY

The present disclosure provides a computer-implemented method for medical image processing. The computer-implemented method includes: acquiring a plurality of frames of medical image data including a reference frame and at least one floating frame; performing image segmentation on the reference frame to obtain a mask for a target region in the reference frame; performing, based on the reference frame and the mask, motion correction on the floating frame to obtain a motion corrected image corresponding to the floating frame.

The computer-implemented present disclosure also provides a computer apparatus including a processor and a memory configured to store a computer program. A method for medical image processing is implemented when the processor executes the computer program. The method includes: acquiring a plurality of frames of medical image data including a reference frame and at least one floating frame, each of the reference frame and the floating frame including a target region and a background region; performing image segmentation on the reference frame to obtain a mask for a target region in the reference frame; performing, based on the reference frame and the mask, motion correction on the floating frame to obtain a motion corrected image corresponding to the floating frame.

The present disclosure further provides a non-volatile computer readable storage medium on which a computer program is stored. A method for medical image processing is implemented when a computer executes the computer program. The method includes: acquiring a plurality of frames of medical image data including a reference frame and at least one floating frame; performing image segmentation on the reference frame to obtain a mask for a target region in the reference frame; performing, based on the reference frame and the mask, motion correction on the floating frame to obtain a motion corrected image corresponding to the floating frame, and performing motion analysis on the target region in the motion corrected image.

BRIEF DESCRIPTION OF THE DRAWINGS

FIG. 2 is a schematic flow diagram illustrating the method for medical image processing according to an embodiment of the present disclosure.

FIG. 3 is a schematic flow diagram illustrating a method for performing image registration on a background region in a floating frame according to an embodiment of the present disclosure.

FIG. 4 is a schematic flow diagram illustrating a method for determining an initial driving force based on a reference frame and the floating frame according to an embodiment of the present disclosure.

DETAILED DESCRIPTION OF THE EMBODIMENTS

Figure 1:
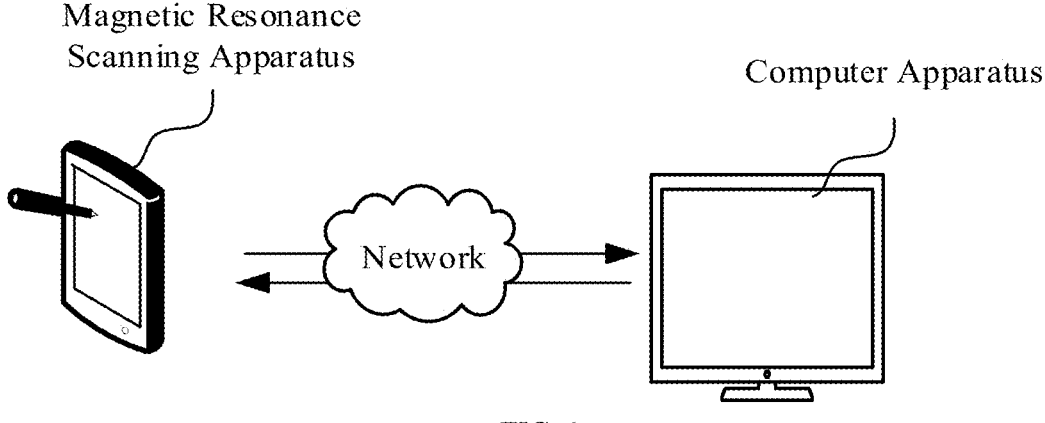
FIG. 1 is a schematic diagram illustrating an application environment of a method for medical image processing according to an embodiment of the present disclosure.

In order to make purposes, technical solutions and advantages of the present disclosure clearer and more understandable, the following is a further detailed description of the present disclosure with reference to the accompanying drawings and embodiments. It is to be understood that the specific embodiments described herein are intended to explain the present disclosure only and are not intended to limit the present disclosure.

An aspect of the present disclosure provides a computer-implemented method for medical image processing. The method includes: acquiring a plurality of frames of medical image data including a reference frame and at least one floating frame; performing image segmentation on the reference frame to obtain a mask for a target region in the reference frame; and performing, based on the reference frame and the mask, motion correction on the floating frame to obtain a motion corrected image corresponding to the floating frame.

In this aspect of the present disclosure, the performing, based on the reference frame and the mask, the motion correction on the updated floating frame includes: determining, based on the reference frame and the floating frame, an initial driving force; determining, based on the initial driving force and the mask, a target driving force; processing the target driving force and the floating frame to obtain the updated floating frame; and performing motion correction on a background region in the updated floating frame.

In this aspect of the present disclosure, the determining the initial driving force includes: acquiring correlation information indicating correlation between pixels in the reference frame and pixels in the floating frame; and performing, based on the correlation information, a negative gradient operation on the floating frame to obtain the initial driving force.

In this aspect of the present disclosure, the correlation information includes a cross-correlation parameter indicating a cross-correlation between a pixel in the reference frame and a corresponding pixel in the floating frame, and the acquiring the correlation information includes: calculating, from pixel values of the pixels in the reference frame and pixel values of the pixels in the floating frame, a variance of the pixel values of the pixels in the reference frame, a variance of the pixel values of the pixels in the floating frame and a covariance between the pixel values of the pixels in the reference frame and the pixel values of the pixels in the floating frame; and determining, for each pixel in the reference frame, the cross-correlation parameter indicating the cross-correlation between the pixel in the reference frame and a corresponding pixel in the floating frame, based on the variance of the pixel values of the pixels in the reference frame, the variance of the pixel values of the pixels in the floating frame and the covariance between the pixel values of the pixels in the reference frame and the pixel values of the pixels in the floating frame.

In this aspect of the present disclosure, the determining the target driving force includes: subtracting a preset standard matrix with the mask to obtain a subtraction result; and multiplying the initial driving force with the subtraction result to obtain the target driving force.

In this aspect of the present disclosure, the processing the target driving force and the floating frame to obtain the updated floating frame includes: performing regularization on the target driving force to determine a deformation field update amount for the floating frame; updating an initial deformation field of the floating frame with the deformation field update amount to obtain the updated deformation field; and resampling, based on the updated deformation field, pixel values of pixels in the floating frame to obtain the updated floating frame.

In this aspect of the present disclosure, the performing the motion correction on the background region in the updated floating frame includes: performing one or more iterative operations. Each iterative operation includes: determining the updated floating frame as a current floating frame; performing, based on the reference frame and the mask, image registration on a background region in the current floating frame to obtain the motion corrected image of the current floating frame; and updating, based on the motion corrected image of the current floating frame, the current floating frame.

In this aspect of the present disclosure, a convergence condition of the iterative operation is that a number of iterations reaches a preset iteration number threshold or a precision of the cross-correlation parameter reaches a preset precision.

In this aspect of the present disclosure, the motion correction is based on rigid protection for a target region of the floating frame.

In this aspect of the present disclosure, the computer-implemented method further includes performing motion analysis on a target region in the motion corrected image.

Another aspect of the present disclosure provides a computer apparatus including a processor and a memory configured to store a computer program. The method as described in the above aspect is implemented when the processor executes the computer program.

A further aspect of the present disclosure provides a non-volatile computer readable storage medium on which a computer program is stored. The method as described in the above aspect is implemented when a computer executes the computer program.

The method for medical image processing provided in the present disclosure is applicable to a computer apparatus in connection with a magnetic resonance scanning apparatus as shown in FIG. 1. Optionally, the magnetic resonance scanning apparatus may be communicatively connected the computer apparatus by a blue-tooth technology, a mobile network, a Wi-Fi technology, or the like. Optionally, the computer apparatus may be, but is not limited to, various personal computers, notebook computers, smartphones, tablet computers and portable wearable devices, and may be realized by an independent server or a server cluster composed of a plurality of servers. The specific form of the computer apparatus is not limited in these embodiments. Optionally, the magnetic resonance scanning apparatus may scan and image a target region, and acquire medical data, and then transmit the medical data to the computer apparatus. The computer apparatus reconstructs the medical data to obtain a reference frame and a floating frame. Optionally, both the reference frame and the floating frame may be at least one of X-ray images, radionuclide images, ultrasound images, magnetic resonance images and the like. The specific process of the method for medical image processing will be described in detail in the following embodiments.

In order to analyze the pathology status of the target region or target organ of the imaging object, it is necessary to protect an image corresponding to other areas or other organs in the medical image of the imaging object, and further analyze the image of the target region or target organ in the medical image to determine the operation status of the target region or target organ, so that the analysis result can be consistent with the analysis result when the other areas or other organs of the imaging object do not move, thereby improving accuracy of the analysis result to help a doctor to analyze the pathology of the imaging object. Based on this, a method for medical image processing is provided in this embodiment. FIG. 2 shows a schematic flow diagram illustrating the method for medical image processing. The method is illustrated by applying it to the computer apparatus in FIG. 1 as an example, and includes the following steps S100 to S400.

In step S100, a plurality of frames of medical image data including the reference frame and at least one floating frame is acquired.

Specifically, the plurality of frames of medical image data correspond to a plurality of medical images. The medical image may be a real-time acquired image of the imaging object, or may be a pre-acquired image of the imaging object stored locally or stored in a cloud. In this embodiment, motion correction may be performed on each of the floating frames by using the reference frame as a reference image.

It should be noted that the reference frame and the floating frame are the medical images corresponding to different physiological phases of the same imaging object in one scan. The reference frame may be a medical image corresponding to a phase with relatively stationary physiological motion.

In step S200, image segmentation is performed on the reference frame to obtain a mask for the target region in the reference frame.

Specifically, an image of the target region and an image of a background region other than the target region is included in the reference frame. The target region may be a region of interest of the imaging object in the medical image, which corresponds to a tissue of interest or an organ of interest of the imaging object, i.e., the target tissue or the target organ. The background region may be a region of non-interest of the imaging object in the medical image. Optionally, the reference frame may be an image in which the target region image and the background region image are combined. The size of the reference frame may be any size as long as the target region image is included in the reference frame.

Optionally, if the target portion or target organ of the imaging object needs to be analyzed to obtain the pathology state, the reference frame may be the medical image including the target portion and other portions around the target portion, or may be the medical image including the target organ and other portions around the target organ.

It will be appreciated that the computer apparatus may perform the image segmentation on the target region in the reference frame by using a threshold-based, region-based, edge-based, and/or neural network-based segmentation method to obtain a segmented image and a mask for the target region in the segmented image. A parameter involved in the segmentation method used may be set according to the target region actually segmented. In this embodiment, a neural network-based segmentation method may be used to implement the image segmentation. Specifically, the neural network model used may be a self-organizing mapping neural network segmentation model, a graph neural network segmentation model, and/or a genetic neural network segmentation model, or the like. In this embodiment, a full-convolutional neural network segmentation model, such as a Vnet segmentation model, may be used to implement the image segmentation. The image segmentation may be based on a trained Vnet segmentation model.

It should be noted that the mask for the target region in the segmented image may be the mask for the target region in the medical image. Optionally, the segmented image may be an image corresponding to the target portion of the imaging object, or may be an image corresponding to the target organ of the imaging organ. Optionally, the reference frame may be a large-area region image including the target portion or the target organ, and correspondingly, the segmented image may be a small-area region image including the target portion or the target organ. Optionally, the size of the segmented image may be the same as the size of the mask for the target region. The mask for the target region may be provide in such a way that in the mask, each of pixels corresponding to the target portion or the target organ to be protected has a pixel value of 1, while each of pixels corresponding to other organs to be corrected has a pixel value of 0.

In this embodiment, the target region is a region where the target organ is located. The target organ may be an organ of the imaging object, for example, heart, intestine, uterus, lung, breast, or other organs where local motion exists. Since the cine magnetic resonance imaging technology can perform fast imaging on the moving organ of the imaging object, in this embodiment, a specific process of the method for medical image processing is described by using an example in which both the reference frame and the floating frame are a cine magnetic resonance image.

In step S300, image registration is performed on the background region in the floating frame based on the reference frame and the mask, to obtain the updated floating frame. The floating frame includes the image of the target region and the image of the background region other than the target region. The registration result, i.e., the registered image may be may be displayed on a screen of a display communicably connected to the computer apparatus.

Specifically, the image to be processed by the image registration may be a locally deformed image. Optionally, the image registration may refer to obtaining spatial alignment between images with the same or different patterns acquired from the same or different subjects, and is widely used in radiation therapy planning, surgical guidance, imaging motion calibration, disease diagnosis, image segmentation, and treatment effect tracking.

It should be noted that, since the motion of the target organ causes local deformation in the corresponding floating frame, the computer apparatus can perform the image registration on the background region in the floating frame based on the reference frame and the mask for the target region in the reference frame to obtain the updated floating frame. Optionally, the floating frame may be one or more medical images acquired in real time, and include the target region and the background region other than the target region. Optionally, the computer apparatus may perform the image registration on the background region image in the floating frame based on the reference frame and the mask for the target region in the reference frame.

It will be appreciated that the image registration may be understood as alignment and matching processing, and also as a process of performing processing such as translation, conversion, rotation, scaling, flipping, operation, or the like on the image to be registered. Optionally, the image to be registered mentioned may be the floating frame.

The translation processing may be understood as a process of moving some or all of the pixels in the image to be registered in a horizontal (x-axis) direction or a vertical (y-axis) direction by a given translation amount. The conversion processing may be understood as a process of converting between some or all of the pixels in the image to be registered and a corresponding coordinate point. The rotation processing may be understood as a process of rotating some or all of the pixels in the image to be registered by a preset angle with an origin as a center of circle; the scaling process may be understood as a process of scaling some or all of the pixels in the image to be registered by a preset multiple in the horizontal (x-axis) direction or the vertical (y-axis) direction; the flipping process may be understood as a process of flipping some or all of the pixels in the image to be registered with the preset axis as the axis of symmetry; and the operation processing may be understood as a process of performing operation processing such as addition, subtraction, multiplication, division, exponent, and/or logarithm, or the like on some or all of the pixels in the image to be registered.

In step S400, based on the updated floating frame, motion correction is performed on the background region in the floating frame to obtain a motion corrected image, and motion analysis is performed on the target region image in the motion corrected image.

Specifically, the motion correction may be understood as processing such as translation, conversion, rotation, scaling, flipping, and operation, or the like. The computer apparatus may perform, based on the updated floating frame, the processing such as translation, conversion, rotation, scaling, flipping, and operation, or the like on the background region image in the floating frame to obtain the motion corrected image. The motion correction is based on rigid protection for the target region of the floating frame. The rigid protection for the target region of the floating frame means that the motion correction is implemented in such a way that non-rigid deformation of the target region of the floating frame during non-rigid registration is restrained. Further, the computer apparatus may also perform the motion analysis on the target region image in the motion corrected image to evaluate the motion situation of the target organ of the imaging object.

For example, if the target organ is the heart, the computer apparatus may further perform the motion analysis on the image of the heart region to evaluate shape and function of the heart of the imaging object. The motion analysis may include ejection fraction calculation, cardiac stress analysis, or the like. If the target organ is another organ, the purpose of the motion analysis is similar.

It should be noted that the motion corrected image may be an image in which the motion correction is performed on the background region in the floating frame and the motion correction is not performed on the target region. Optionally, the target region in the motion corrected image may be the same as the target region in the floating frame, but the background region in the motion corrected image is different from the background region in the floating frame. In this embodiment, the floating frame may be understood as an image to be corrected. The motion corrected image may be displayed on a screen of a display communicably connected to the computer apparatus.

In the method for medical image processing, the computer apparatus can acquire a plurality of frames of medical image data, perform the image segmentation on the reference frame in the plurality of frames of medical image data to obtain the mask for the target region in the reference frame, perform the image registration on the background region in the floating frame in the plurality of frames of medical image data based on the reference frame and the mask to obtain the updated floating frame, perform the motion correction on the background region in the floating frame based on the updated floating frame to obtain the motion corrected image, and perform the motion analysis on the target region in the motion corrected image. In this method, the respiratory motion of the target organ image in the floating frame may be protected by the respiratory motion of the other organ images in the floating frame so that the respiratory motion of the target organ image in the floating frame can be kept unchanged, and therefore accurate basic information for the next analysis of the motion situation of the target organ is provided. Meanwhile, in this method, the motion corrected image corresponding to the target organ in the floating frame can be acquired without affecting free breathing of the imaging object, no breathing difficulty for the imaging subject is caused, the motion corrected image corresponding to the target organ in the floating frame can be determined by directly performing a series of processing on the reference frame and the floating frame of the imaging object in the free breathing state, and therefore the general applicability of the breathing motion correction method can be improved. Moreover, in this method, the motion corrected image corresponding to the target organ in the floating frame can be determined by direct processing of the real medical image, and the motion correction can be realized without other information, so that the motion condition of the target organ in the motion corrected image is consistent with the real motion state of the target organ of the imaging object, and therefore the accuracy of the respiratory motion corrected image acquired is improved. In addition, in this method, the motion analysis may be further performed on the target region image in the motion corrected image to evaluate the motion condition of the target organ of the imaging object.

In order to perform the motion correction on the floating frame, it is necessary to perform the image registration on the floating frame first. Therefore, in an embodiment, as shown in FIG. 3, for each of the floating frames, the step S200 where the image registration is performed on the background region image in the floating frame based on the reference frame and the mask to obtain the updated floating frame, can be implemented by the following steps S210 to S230.

In step S210, an initial driving force is determined based on the reference frame and the floating frame.

Specifically, the computer apparatus may perform first operation processing on the pixel value of some or all of the pixels in the reference frame and the pixel value of some or all of the pixels the floating frame to obtain the initial driving force $f_1$.

It should be noted that the first operation processing may be operation processing such as addition, subtraction, multiplication, division, exponent, square root, quadrate, and/or logarithm, or the like. Optionally, the initial driving force $f_1$ may be understood as a deformation amount of the target organ and the other organs in the reference frame and the floating frame. Optionally, a size of the initial driving force $f_1$, a size of the reference frame, and a size of the floating frame may all be the same.

In step S220, a target driving force is determined based on the initial driving force and the mask.

Specifically, the computer apparatus may perform second operation processing on the initial driving force $f_1$ and the mask for the target region in the reference frame to obtain the target driving force $f_2$. Optionally, the second operation processing may be the same as or different from the first operation processing.

In step S230, the target driving force and the floating frame are processed to obtain the updated floating frame.

It should be noted that the computer apparatus may perform processing such as third operation processing, comparison processing, convolution processing, and/or data conversion processing, or the like, on the target driving force and the floating frame to obtain the updated floating frame. The third operation processing may be the same as or different from the second operation processing and the first operation processing mentioned above.

In the method for medical image processing the initial driving force can be determined based on the reference frame and the floating frame, the target driving force is determined based on the initial driving force and the mask, and the target driving force and the floating frame is processed to obtain the updated floating frame. In this method, the target organ image in the floating frame can be protected by the mask for the target region to improve the accuracy of the result of the motion analysis of the target region image in the floating frame.

In an embodiment, as shown in FIG. 4, the step S210 where the initial driving force is determined based on the reference frame and the floating frame may include the following steps S211 to S212.

In step S211, correlation information indicating correlation between pixels in the reference frame and pixels in the floating frame is obtained.

Specifically, in this embodiment, the motion correction may be performed on one or more floating frames. Therefore, for each of the floating frames, the computer apparatus may perform the operation processing on the reference frame and the floating frame respectively by using a mean square error method, a mutual information method, a cross-correlation coefficient method, or a local cross-correlation coefficient method, to obtain the correlation information indicating the correlation between the pixels in the reference frame and the pixels in the floating frame. Optionally, the operation processing may be operation processing such as addition, subtraction, multiplication, division, exponent, square root, quadrate, and/or logarithm, or the like.

The correlation indicated by the correlation information may be understood as similarity between each pixel in the reference frame and the pixels in the floating frame.

The following will describe a process of calculating the correlation information between the pixels in the reference frame and the pixels in the floating frame by using the local correlation information method. In an embodiment, the correlation information includes a cross-correlation parameter indicating a cross-correlation between a pixel in the reference frame and a corresponding pixel in the floating frame. And the step S211 where the correlation information indicating the cross-correlation between the pixels in the reference frame and the pixels in the floating frame is acquired, may include: calculating, from pixel values of the pixels in the reference frame and pixel values of the pixels in the floating frame, a variance of the pixel values of the pixels in the reference frame, a variance of the pixel values of the pixels in the floating frame and a covariance between the pixel values of the pixels in the reference frame and the pixel values of the pixels in the floating frame; and determining, for each pixel in the reference frame, the cross-correlation parameter indicating the cross-correlation between the pixel in the reference frame and a corresponding pixel in the floating frame, based on the variance of the pixel values of the pixels in the reference frame, the variance of the pixel values of the pixels in the floating frame and the covariance between the pixel values of the pixels in the reference frame and the pixel values of the pixels in the floating frame.

The computer apparatus may perform operation processing on the covariance between the pixel values of the pixels in the reference frame and the pixel values of the pixels in the floating frame, the variance of the pixel values of the pixels in the reference frame, and the variance of the pixel values of the pixels in the floating frame to obtain the cross-correlation parameter lcc between each pixel in the reference frame and the corresponding pixel in the floating frame. The operation processing may also be operation processing such as addition, subtraction, multiplication, division, exponent, square root, quadrate, and/or logarithm, or the like.

In this embodiment, if the reference frame is for example, Frame 1, and the floating frame is for example, Frame 2, the computer apparatus may calculate the variance of pixel values of all pixels in the Frame 1 and the variance of pixel values of all pixels in the Frame 2, respectively, as $v_1$ and $v_2$, calculate the covariance $Cov_{1,2}$ between the pixel values of the pixels in Frame 1 and the pixel values of the pixels the Frame 2, and then calculate the cross-correlation parameters $lcc_{1,2}=Cov^2_{1,2}/(v_1*v_2)$ indicating the cross-correlation between each pixel in the reference frame and the corresponding pixel in the floating frame. For each of the floating frames, the cross-correlation parameters indicating the cross-correlation between the reference frame and the floating frame may be respectively calculated in the manner.

In step S212, a negative gradient operation is performed on the floating frame based on the correlation information to obtain the initial driving force.

Specifically, for each of the floating frames, the computer apparatus can calculate the negative gradient direction derivative of the floating frame (i.e., negative gradient operation) based on the cross-correlation parameter indicating the cross-correlation between the reference frame and the floating frame, to obtain the initial driving force $f_1$ corresponding to the floating frame.

In the method for medical image processing, the correlation information indicating the cross-correlation between the pixels in the reference frame and the pixels in the floating frame can be acquired, the negative gradient operation is performed on the floating frame based on the correlation information to obtain the initial driving force, and the target driving force is determined based on the initial driving force, so that motion correction is performed on the floating frame based on the target driving force, and the accuracy of the result of the motion correction is improved.

Figure 5:
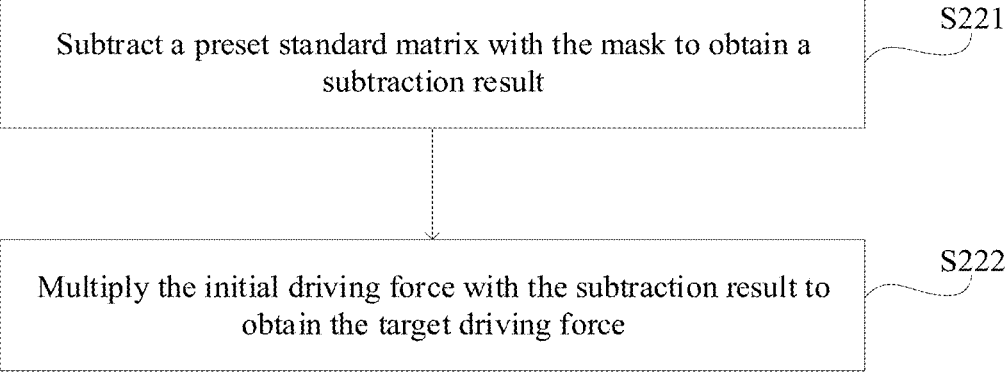
FIG. 5 is a schematic flow diagram illustrating a method for determining a target driving force based on the initial driving force and a mask according to an embodiment of the present disclosure.

In an embodiment, as shown in FIG. 5, the step S220 where the initial driving force is determined based on the reference frame and the floating frame, may include:

In step S221, a preset standard matrix is subtracted with the mask to obtain a subtraction result.

Specifically, the preset standard matrix may be a constant matrix whose size is the same as the size of the mask for the target region in the reference frame. Optionally, values of all elements in the standard matrix may be the same or different. The value of each element in the standard matrix can be any value, but in this embodiment, the value of each element in the standard matrix is 1.

It should be noted that the computer apparatus can subtract the preset standard matrix with the mask for the target region in the reference frame to obtain the subtraction result. Optionally, the subtraction result may be in a matrix form, and the size of the subtraction result may be the same as the size of the mask for the target region in the reference frame.

In step S222, the initial driving force is multiplied with the subtraction result to obtain the target driving force.

It should be noted that the computer apparatus can perform the multiplication on the initial driving force and the numerical value at the corresponding position of the subtraction result to obtain the target driving force. Optionally, the size of the target driving force may be the same as the size of the initial driving force. The numerical value at the corresponding position of the target driving force may be equal to a result of multiplying the initial driving force by the numerical value at the corresponding position of the subtraction result.

In the method for medical image processing, the target driving force is determined based on the initial driving force, and the motion correction is performed on the floating frame based on the target driving force, so that the accuracy of the result of the motion correction is improved.

Figure 6:
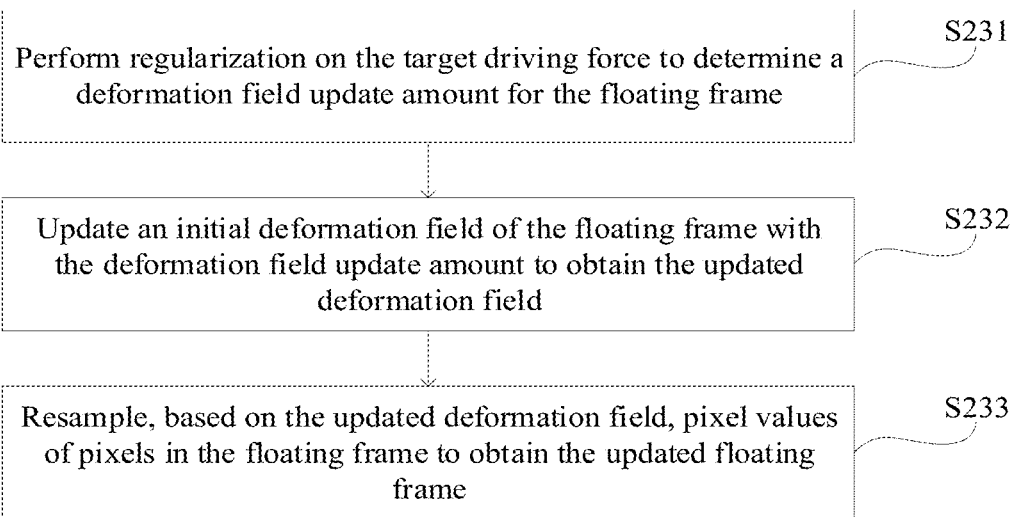
FIG. 6 is a schematic flow diagram illustrating a method for processing the target driving force and the floating frame to obtain the updated floating frame according to an embodiment of the present disclosure.

The following will describe a process of acquiring the updated floating frame. In this embodiment, as shown in FIG. 6, the step S230 where the target driving force and the floating frame are processed to obtain the updated floating frame may include the following steps S231 to S233.

In step S231, regularization is performed on the target driving force to determine a deformation field update amount for the floating frame.

Specifically, the computer apparatus can perform regularization on the target driving force $f_2$ to obtain the deformation field update amount u for the floating frame. Optionally, the deformation field update amount u of the floating frame can be understood as a variation of the deformation field s of the target organ in the case of motion. In this embodiment, the size of the deformation field update amount u of the floating frame is the same as the size of the floating frame.

It should be noted that the regularization can include operation processing such as addition, subtraction, multiplication, division, exponent operation, logarithm operation, and the like. However, in this embodiment, the regularization is a convolution operation. Specifically, the computer apparatus may perform the convolution operation on the target driving force $f_2$ and the convolution kernel k to obtain the deformation field update amount u of the floating frame. The deformation field update amount u of the floating frame is equal to $f_2 \otimes k$. Optionally, the convolution kernel k can be a transposed convolution kernel, a separable convolution kernel, a hole convolution kernel, or the like. However, in this embodiment, the convolution kernel k is a Gaussian convolution kernel.

In step S232, the initial deformation field of the floating frame is updated with the deformation field update amount to obtain the updated deformation field.

Specifically, the computer apparatus may perform an arithmetic operation on the deformation field update amount u and the initial deformation field $s_1$ of the floating frame to implement an update process to obtain the updated deformation field $s_2$. In this embodiment, the updated deformation field $s_2$ is obtained by adding the deformation field update amount u and the initial deformation field $s_1$ of the floating frame, i.e., the updated deformation field $s_2$ is equal to $s_1+u$. Optionally, the value of the initial deformation field $s_1$ of the floating frame is the same as the value of the updated deformation field $s_2$.

In step S233, pixel values of pixels in the floating frame is resampled based on the updated deformation field to obtain the updated floating frame.

In this embodiment, the value of the deformation field update amount $s_2$ is the same as the value of the floating frame. Optionally, the computer apparatus can perform fourth operation processing on the updated deformation field $s_2$ and the pixel value in the floating frame to obtain the updated floating frame. Optionally, the fourth operation processing may be the same as or different from the third operation processing, the second operation processing and the first operation processing mentioned above. However, in this embodiment, the fourth operation processing is the addition.

The computer apparatus can perform addition on each numerical value in the updated deformation field $s_2$ and the pixel value at the corresponding position in the floating frame to obtain an addition sum corresponding to each position in the floating frame, and combine the addition sum at all positions according to the corresponding position to obtain the updated floating frame.

In the method for medical image processing, the target driving force and the floating frame can be processed to obtain the updated floating frame, and therefore registration of the floating frame is implemented to further improve the accuracy of the result of motion analysis on the target region image in the floating frame. Also, in the method, the overfitting processing of the target driving force can be eliminated by the regularization, and therefore the accuracy of the motion correction result can be improved.

In order to protect the target organ image in the floating frame and enable to accurately perform the motion correction on the background area images in floating frames, in an embodiment, the step S300 where the motion correction is performed on the background region in the updated floating frame may include performing one or more iterative operations.

Each iterative operation includes: determining the updated floating frame as a current floating frame; performing, based on the reference frame and the mask, image registration on the background region in the current floating frame to obtain the motion corrected image of the current floating frame; and updating, based on the motion corrected image of the current floating frame. A convergence condition of the iterative operation is that a number of iterations reaches a preset iteration number threshold or a precision of the cross-correlation parameter reaches a preset precision.

It should be noted that the computer apparatus can determine the updated floating frame acquired as the current floating frame, perform the image registration on the background region in the current floating frame to obtain the updated current floating frame, and determining the updated current floating frame as the motion corrected image of the current floating frame if the current number of iterations reaches the preset number threshold or the precision of the current cross-correlation parameter reaches the preset precision.

It will be appreciated that if the current number of iterations does not reach the preset number threshold and the precision of the current cross-correlation parameter does not reach the preset precision, the motion corrected image of the current floating frame can be determined as the current floating frame, and for the current floating frame, the step of performing the image registration on the background region in the current floating frame based on the reference frame and the mask is continued until the current number of iterations reaches the preset number threshold or the precision of the current cross-correlation parameter reaches the preset precision. And then the iterative operation ends, and the updated current floating frame is determined as the motion corrected image of the current floating frame. The motion corrected image is an image in which the target region in the current floating frame is protected and the background region in the current floating frame is motion corrected.

In this embodiment, the iterative operation may be understood as a process of the step S300 being repeated for the current floating frame until the number of iterations is equal to the preset iteration number threshold or the accuracy of the obtained cross-correlation parameter is equal to the preset accuracy, and the iterative operation ends.

It will be appreciated that for each of the floating frames, the initial deformation field $s_1$ is 0, and when the next iteration operation is performed, the initial deformation field $s_1$ is equal to the updated deformation field $s_2$.

Figure 7:
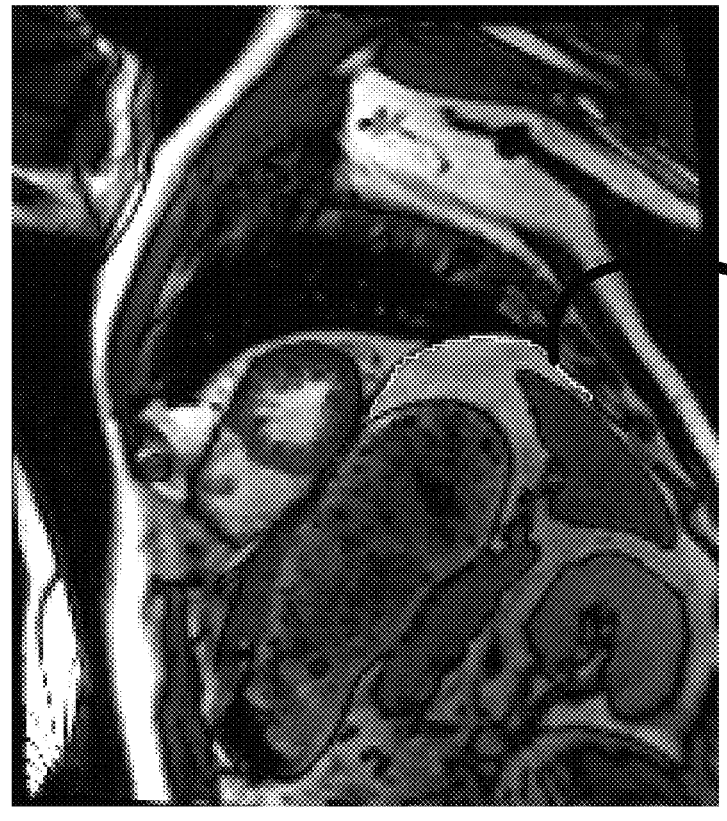
FIG. 7 showing the floating frame including a heart region according to an embodiment of the present disclosure.
Figure 8:
FIG. 8 is an image corresponding to a motion offset of FIG. 7.
Figure 9:
FIG. 9 is an image after motion correction being performed on FIG. 8.
Figure 10:
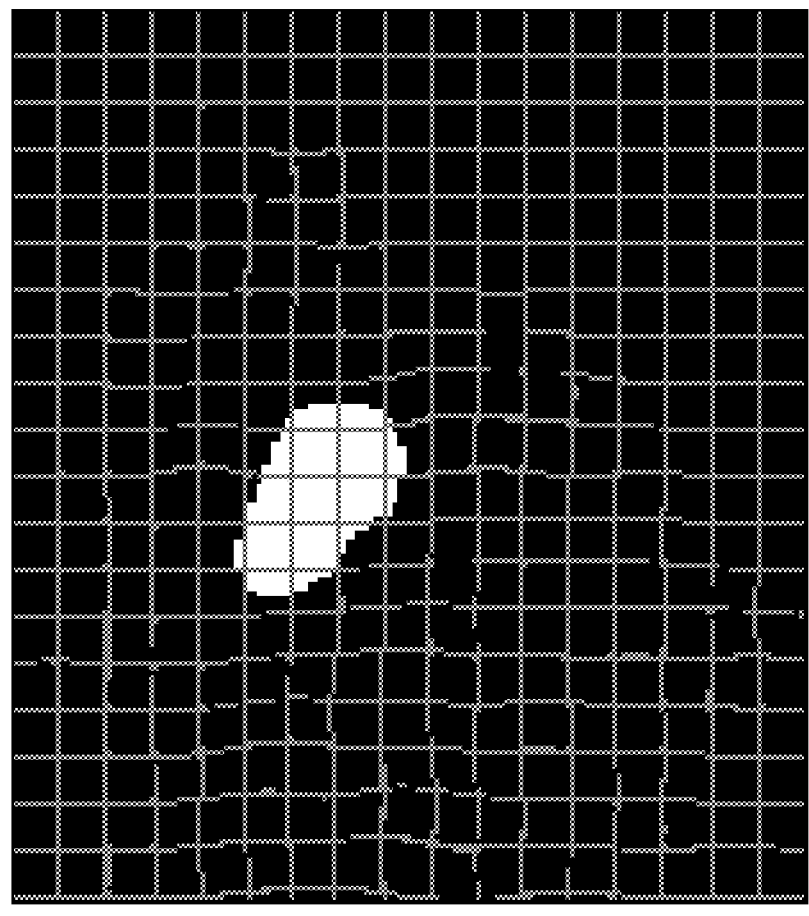
FIG. 10 is a deformation image corresponding to FIG. 8.

Illustratively, the floating frame is an image including the heart region. FIG. 7 shows the reference frame including the heart region. The reference frame is an image in which there is no motion offset in a diaphragm region below the heart. A white curve in the middle of FIG. 7 indicates a diaphragm region boundary line, and an image with motion offset in the diaphragm region below the heart region before the motion correction is performed on the diaphragm region in the floating frame shown in FIG. 7 is shown in FIG. 8 (the white curve in the middle of FIG. 8 indicates an offset line in which the diaphragm region causes diaphragm region boundary line to be shifted due to the motion offset). Correspondingly, FIG. 9 shows the motion corrected image obtained after the motion correction is performed on the floating frame; FIG. 9 is substantially consistent with FIG. 7, i.e., after the motion correction is performed on the diaphragm region in FIG. 8, the diaphragm region boundary substantially consistent with the diaphragm region boundary in the reference frame. In addition, FIG. 10 shows a deformation image corresponding to FIG. 8. A square grid in FIG. 10 indicates a region in which there is no motion deformation, a deformed grid indicates a region in which motion deformation occurs, and a white region indicates a heart region. In this embodiment, the heart region in the floating frame is protected, and the motion correction is performed on the diaphragm region.

In the method for medical image processing, the optimal updated floating frame can be obtained by iterative loop processing, and the optimal updated floating frame is determined as the motion corrected image of the floating frame. In this method, not only a motion effect on the background area of the floating frame can be corrected, but also the motion of the target region can be protected, and therefore the general applicability of the respiratory motion correction method is improved. In addition, in this method, the motion corrected image corresponding to the target organ in the floating frame can be determined by direct processing of the real medical image, the motion correction can be realized without other information, and therefore the motion condition of the target organ in the motion corrected image is consistent with a real motion state of the target organ of the imaging object, and the accuracy of the respiratory motion corrected image acquired is improved.

In order to facilitate the understanding of those of ordinary skill in the art, the method for medical image processing provided in the present disclosure is described with an example in which the executive object is the computer apparatus. Specifically, the method includes the following steps.

(1) A plurality of frames of medical image data including a reference frame and at least one floating frame are acquired.

(2) Image segmentation is performed on the reference frame to obtain a mask for the target region in the reference frame.

For each of the floating frames, the following steps are executed.

(3) A variance of the pixel values of the pixels in the reference frame, a variance of the pixel values of the pixels in the floating frame and a covariance between the pixel values of the pixels in the reference frame and the pixel values of the pixels in the floating frame are calculated from the pixel values of the pixels in the reference frame and the pixel values of the pixels in the floating frame.

(4) A cross-correlation parameter indicating a cross-correlation between the pixel in the reference frame and a corresponding pixel in the floating frame is determined based on the variance of the pixel values of the pixels in the reference frame, the variance of the pixel values of the pixels in the floating frame and the covariance between the pixel values of the pixels in the reference frame and the pixel values of the pixels in the floating frame.

(5) The negative gradient operation is performed on the floating frame based on the correlation information to obtain the initial driving force.

(6) A preset standard matrix is subtracted with the mask to obtain a subtraction result.

(7) The initial driving force is multiplied with the subtraction result to obtain the target driving force.

(8) Regularization is performed on the target driving force to determine the deformation field update amount of the floating frame.

(9) The initial deformation field of the floating frame is updated with the deformation field update amount to obtain an updated deformation field.

(10) The pixel values of the pixels in the floating frame is resampled based on the updated deformation field to obtain the updated floating frame.

Specifically, addition is performed on the numerical values in the updated deformation field and the pixel values of the pixels in the floating frame to obtain the updated floating frame.

(11) The updated floating frame is determined as the current floating frame, and the steps (3) to (10) continue to be iteratively executed for the current floating frame. The convergence condition of the iterative operation is that the number of iterations reaches the preset number threshold or the precision of the cross-correlation parameter reaches a preset precision.

The detail execution process of the steps (1) to (11) can be referred to the description of the embodiments, and the implementation principles and the technical effects thereof are similar, and will not be repeated again.

It should be understood that although the steps in the flowcharts of FIGS. 2-6 are shown sequentially as indicated by arrows, these steps are not necessarily executed sequentially as indicated by arrows. Unless explicitly stated herein, these steps are not executed in a strict order and may be executed in other orders. Moreover, at least a part of the steps in FIGS. 2-6 may include a plurality of steps or stages, the steps or the stages are not necessarily executed at the same time, but may be executed at different times, and the execution order of the steps or the stages is not necessarily executed sequentially, but may be executed alternately with other steps or at least a part of the steps or stages in other steps.

Figure 11:
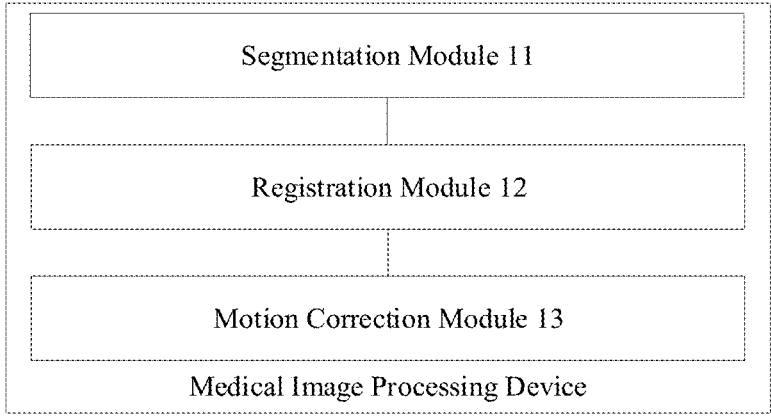
FIG. 11 is a structural block diagram illustrating a device for medical image processing according to an embodiment of the present disclosure.

In an embodiment, as shown in FIG. 11, a device for medical image processing is provided. The device for medical image processing includes an image acquisition module 11, a segmentation module 12, a registration module 13, and a motion correction module 14.

The image acquisition module 11 is configured to acquire a plurality of frames of medical image data including a reference frame and at least one floating frame. Each of the reference frame and the floating frame including a target region and a background region.

The segmentation module 12 is configured to perform image segmentation on the reference frame to obtain a mask for the target region in the reference frame.

The registration module 13 is configured to perform image registration on the background region in the floating frame based on the reference frame and the mask to obtain an updated floating frame.

The motion correction module 14 is configured to perform motion correction on the background region in the updated floating frame to obtain a motion corrected image corresponding to the floating frame, and perform motion analysis on the target region image in the motion corrected image.

The device for medical image processing provided in this embodiment can execute the methods describe in the above embodiments, and the implementation principles and technical effects thereof are similar, and will not be repeated again.

In an embodiment, the image registration module 13 includes an initial driving force determining unit, a target driving force determining unit, and a processing unit.

The initial driving force determining unit is configured to determine an initial driving force based on the reference frame and the floating frame.

The target driving force determining unit is configured to determine a target driving force based on the initial driving force and the mask.

The processing unit is configured to process the target driving force and the floating frame to obtain the updated floating frame.

In an embodiment, the initial driving force determining unit includes a processing subunit and a negative gradient operation subunit.

The processing subunit is configured to acquire a cross-correlation correlation coefficient indicating a cross-correlation between pixels in the reference frame and pixels in the floating frame.

The negative gradient operation subunit is configured to perform a negative gradient operation on the floating frame based on the cross-correlation correlation coefficient to obtain the initial driving force.

In an embodiment, the processing subunit is configured to calculate, from pixel values of the pixels in the reference frame and pixel values of the pixels in the floating frame, a variance of the pixel values of the pixels in the reference frame, a variance of the pixel values of the pixels in the floating frame and a covariance between the pixel values of the pixels in the reference frame and the pixel values of the pixels in the floating frame, and determine, for each pixel in the reference frame, a cross-correlation parameter indicating a cross-correlation between the pixel in the reference frame and a corresponding pixel in the floating frame, based on the variance of the pixel values of the pixels in the reference frame, the variance of the pixel values of the pixels in the floating frame and the covariance between the pixel values of the pixels in the reference frame and the pixel values of the pixels in the floating frame.

In an embodiment, the target driving force determining unit includes a subtraction subunit and a multiplication subunit.

The subtraction subunit is configured to subtract a preset standard matrix with the mask to obtain a subtraction result.

The multiplication subunit is configured to multiply the initial driving force with the subtraction result to obtain the target driving force.

In an embodiment, the processing unit includes a regularization subunit, a deformation field update subunit and a resampling subunit.

The regularization subunit is configured to perform regularization on the target driving force to determine a deformation field update amount for the floating frame.

The deformation field update subunit is configured to update an initial deformation field of the floating frame with the deformation field update amount to obtain the updated deformation field.

The resampling subunit is configured to resample pixel values of pixels in the floating frame based on the updated deformation field to obtain the updated floating frame.

In an embodiment, the motion correction module 14 includes an iterative processing unit.

The iterative processing unit is configured to determine the updated floating frame as a current floating frame, perform image registration on the background region in the current floating frame based on the reference frame and the mask to obtain the motion corrected image of the current floating frame, and update the current floating frame based on the motion corrected image of the current floating frame. A convergence condition of the iterative operation is that a number of iterations reaches the preset number threshold or a precision of the cross-correlation parameter reaches a preset precision.

The device for medical image processing provided in this embodiment can execute the methods described in the embodiments, and the implementation principles and technical effects thereof are similar, and will not be repeated again.

A specific definition of the device for medical image processing can be referred to the definition of the method for medical image processing, and will not be repeated herein. Each module in the device for medical image processing can be implemented in whole or in part by software, hardware, and combinations thereof. The modules may be embedded in or independent of the processor of the computer apparatus in a form of hardware, or may be stored in the memory of the computer apparatus in a form of software, to facilitate the processor calling and executing the operation corresponding to each of the above modules.

Figure 12:
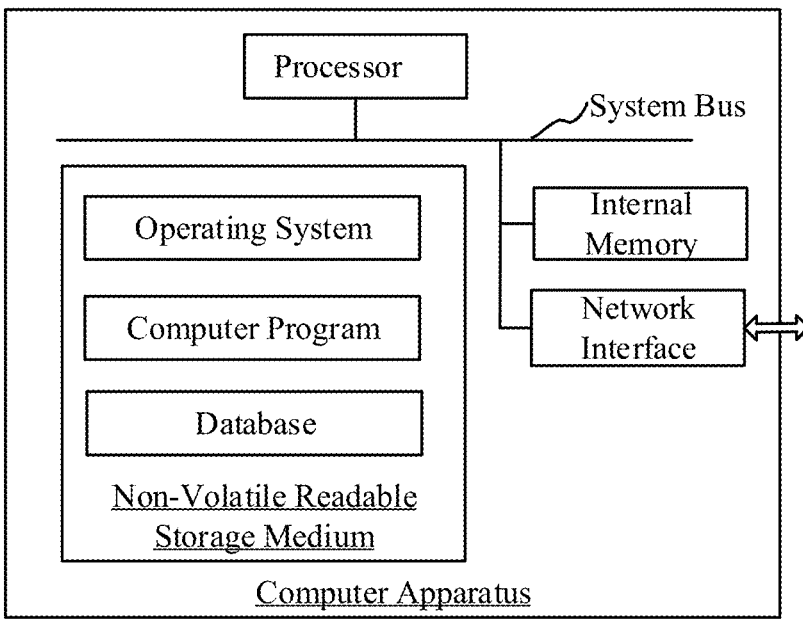
FIG. 12 is a schematic diagram illustrating an internal configuration of a computer apparatus according to an embodiment of the present disclosure.

In an embodiment, a computer apparatus, which may be a server, is provided. FIG. 12 illustrates an internal configuration of the computer apparatus. The computer apparatus includes a processor, a memory, and a network interface which are connected by a system bus. The processor of the computer apparatus is configured to provide computing and control capabilities. The memory of the computer apparatus includes a non-volatile storage medium and an internal memory. The non-volatile storage medium stores an operating system, a computer program, a database and the like. The internal memory provides an environment for the operation of the operating system and the computer program in the non-volatile storage medium. The database of the computer apparatus is configured to store the medical image, the image frame and the image frame to be corrected. The network interface of the computer apparatus is configured to communicate with an external endpoint by a network connection. The computer program is executed by the processor to implement the method for medical image processing.

It will be appreciated by those of ordinary skill in the art that the configuration shown in FIG. 12 is only a block diagram illustrating part of the configuration associated with the embodiments of the present disclosure, and does not constitute a definition of the computer apparatus to which the embodiments of the present disclosure is applied, and the specific computer apparatus may include more or less components than those shown in the figures, or may combine certain components, or may have a different component arrangement.

In an embodiment, a computer apparatus is provided, and includes a processor and a memory configured to store a computer program. The processor configured to execute the computer program to implement the following steps: acquiring a plurality of frames of medical image data including a reference frame and at least one floating frame, each of the reference frame and the floating frame including a target region and a background region; performing image segmentation on the reference frame to obtain a mask for the target region in the reference frame; performing, based on the reference frame and the mask, image registration on the background region in the floating frame to obtain an updated floating frame; and performing motion correction on the background region in the updated floating frame to obtain a motion corrected image corresponding to the floating frame, and performing motion analysis on the target region in the motion corrected image. A corresponding region of the region of interest in the motion corrected image is consistent with a corresponding region of the region of interest in the floating frame.

In an embodiment, a non-volatile computer readable storage medium is provided. A computer program is stored on the non-volatile computer readable storage medium, and when executed by a computer, the computer is caused to implement the following steps: acquiring a plurality of frames of medical image data including a reference frame and at least one floating frame, each of the reference frame and the floating frame including a target region and a background region; performing image segmentation on the reference frame to obtain a mask for the target region in the reference frame; performing, based on the reference frame and the mask, image registration on the background region in the floating frame to obtain an updated floating frame; and performing motion correction on the background region in the updated floating frame to obtain a motion corrected image corresponding to the floating frame, and performing motion analysis on the target region in the motion corrected image.

In an embodiment, a computer program product is provided. The computer program product includes a computer program. The computer program, when executed by a processor, causes the processor to implement the following steps: acquiring a plurality of frames of medical image data including a reference frame and at least one floating frame, each of the reference frame and the floating frame including a target region and a background region; performing image segmentation on the reference frame to obtain a mask for the target region in the reference frame; performing, based on the reference frame and the mask, image registration on the background region in the floating frame to obtain an updated floating frame; and performing motion correction on the background region in the updated floating frame to obtain a motion corrected image corresponding to the floating frame, and performing motion analysis on the target region in the motion corrected image.

Those of ordinary skill in the art may understand that all or part of the processes in the method of the above embodiments may be completed by instructing relevant hardware by the computer program, and the computer program may be stored in a non-transitory computer readable storage medium. When the computer program is executed, the processes of the above methods in the embodiments may be included. Any reference to the memory, the storage, the database or other medium used in various embodiments provided in the present disclosure may include a non-transitory memory and/or a transitory memory. The non-transitory memory may include a read only memory (ROM), a programmable ROM (PROM), an electrically programmable ROM (EPROM), an electrically erasable programmable ROM (EEPROM) or a flash memory. The transitory memory may include a random access memory (RAM) or an external cache memory. As illustration rather than limitation, the RAM is available in a variety of forms, such as a static RAM (SRAM), a dynamic RAM (DRAM), a synchronous DRAM (SDRAM), a dual data rate SDRAM (DDRS-DRAM), an enhanced SDRAM (ESDRAM), a synchlink DRAM (SLDRAM), a rambus direct RAM (RDRAM), a direct rambus dynamic RAM (DRDRAM), a rambus dynamic RAM (RDRAM), and the like.

The technical features of the above embodiments can be combined arbitrarily. To simplify the description, not all possible combinations of the technical features in the above embodiments are described. However, all of the combinations of these technical features should be considered as within the scope of this disclosure, as long as such combinations do not contradict with each other.

The above describe embodiments merely represent several embodiments of the present disclosure, and the description thereof is more specific and detailed, but it should not be construed as limiting the scope of the present disclosure. It should be noted that, several modifications and improvements may be made for those of ordinary skill in the art without departing from the concept of the present disclosure, and these are all within the protection scope of the present disclosure. Therefore, the protection scope of the present disclosure shall be subject to the appended claims.

What is claimed is:

1. A computer-implemented method for medical image processing, the method comprising:

acquiring a plurality of frames of medical image data including a reference frame and at least one floating frame, each of the reference frame and at least one floating frame including a target region for a target organ, and a background region for other organs around the target organ;

performing image segmentation on the reference frame to obtain a mask for a target region in the reference frame; and performing, based on the reference frame and the mask, motion correction on the floating frame to obtain a motion corrected image corresponding to the floating frame, wherein the performing, based on the reference frame and the mask, the motion correction on the floating frame comprises:

determining, based on the reference frame and the floating frame, an initial driving force, the initial driving force representing an amount of a deformation of the target organ and the other organs in the floating frame with respect to the reference frame;

determining, based on the initial driving force and the mask, a target driving force;

processing the target driving force and the floating frame to obtain an updated floating frame; and performing motion correction on the background region in the updated floating frame; and wherein the motion corrected image is an image in which the motion correction has been performed on the background region in the updated floating frame but the motion correction has not been performed on the target region in the updated floating frame.

2. The computer-implemented method of claim 1, wherein the determining the initial driving force comprises:

acquiring correlation information indicating correlation between pixels in the reference frame and pixels in the floating frame; and performing, based on the correlation information, a negative gradient operation on the floating frame to obtain the initial driving force.

3. The computer-implemented method of claim 2, wherein the correlation information comprises a cross-correlation parameter indicating a cross-correlation between a pixel in the reference frame and a corresponding pixel in the floating frame, and the acquiring the correlation information comprises:

calculating, from pixel values of the pixels in the reference frame and pixel values of the pixels in the floating frame, a variance of the pixel values of the pixels in the reference frame, a variance of the pixel values of the pixels in the floating frame and a covariance between the pixel values of the pixels in the reference frame and the pixel values of the pixels in the floating frame; and determining, for each pixel in the reference frame, the cross-correlation parameter indicating the cross-correlation between the pixel in the reference frame and a corresponding pixel in the floating frame, based on the variance of the pixel values of the pixels in the reference frame, the variance of the pixel values of the pixels in the floating frame and the covariance between the pixel values of the pixels in the reference frame and the pixel values of the pixels in the floating frame.

4. The computer-implemented method of claim 1, wherein the determining the target driving force comprises:

subtracting a preset standard matrix with the mask to obtain a subtraction result; and multiplying the initial driving force with the subtraction result to obtain the target driving force.

5. The computer-implemented method of claim 1, wherein the processing the target driving force and the floating frame to obtain the updated floating frame comprises:

performing regularization on the target driving force to determine a deformation field update amount of the floating frame;

updating an initial deformation field of the floating frame with the deformation field update amount to obtain the updated deformation field; and resampling, based on the updated deformation field, pixel values of pixels in the floating frame to obtain the updated floating frame.

6. The computer-implemented method of claim 1, wherein the performing the motion correction on the background region in the updated floating frame comprises:

performing one or more iterative operations, each iterative operation comprising:

determining the updated floating frame as a current floating frame;

performing, based on the reference frame and the mask, image registration on a background region in the current floating frame to obtain the motion corrected image of the current floating frame; and updating, based on the motion corrected image of the current floating frame, the current floating frame.

7. The computer-implemented method of claim 6, wherein a convergence condition of the iterative operation is that a number of iterations reaches a preset iteration number threshold or a precision of the cross-correlation parameter reaches a preset precision.

8. The computer-implemented method of claim 1, wherein the motion correction is based on rigid protection for a target region of the floating frame.

9. The computer-implemented method of claim 1, further comprising:

performing motion analysis on a target region in the motion corrected image.

10. A computer apparatus comprising a processor and a memory configured to store a computer program, wherein a method for medical image processing is implemented when the processor executes the computer program, the method comprising:

acquiring a plurality of frames of medical image data including a reference frame and at least one floating frame, each of the reference frame and at least one floating frame including a target region for a target organ, and a background region for other organs around the target organ;

performing image segmentation on the reference frame to obtain a mask for a target region in the reference frame; and performing, based on the reference frame and the mask, motion correction on the floating frame to obtain a motion corrected image corresponding to the floating frame, wherein the performing, based on the reference frame and the mask, the motion correction on the floating frame comprises:

determining, based on the reference frame and the floating frame, an initial driving force, the initial driving force representing an amount of a deformation of the target organ and the other organs in the floating frame with respect to the reference frame;

determining, based on the initial driving force and the mask, a target driving force;

processing the target driving force and the floating frame to obtain an updated floating frame; and performing motion correction on the background region in the updated floating frame; and wherein the motion corrected image is an image in which the motion correction has been performed on the background region in the updated floating frame but the motion correction has not been performed on the target region in the updated floating frame.

11. The computer apparatus of claim 10, wherein the determining the initial driving force comprises:

acquiring correlation information indicating correlation between pixels in the reference frame and pixels in the floating frame; and performing, based on the correlation information, a negative gradient operation on the floating frame to obtain the initial driving force.

12. The computer apparatus of claim 11, wherein the correlation information comprises a cross-correlation parameter indicating a cross-correlation between a pixel in the reference frame and a corresponding pixel in the floating frame, and the acquiring the correlation information comprises:

calculating, from pixel values of the pixels in the reference frame and pixel values of the pixels in the floating frame, a variance of the pixel values of the pixels in the reference frame, a variance of the pixel values of the pixels in the floating frame and a covariance between the pixel values of the pixels in the reference frame and the pixel values of the pixels in the floating frame; and determining, for each pixel in the reference frame, the cross-correlation parameter indicating the cross-correlation between the pixel in the reference frame and a corresponding pixel in the floating frame, based on the variance of the pixel values of the pixels in the reference frame, the variance of the pixel values of the pixels in the floating frame and the covariance between the pixel values of the pixels in the reference frame and the pixel values of the pixels in the floating frame.

13. The computer apparatus of claim 10, wherein the determining the target driving force comprises:

subtracting a preset standard matrix with the mask to obtain a subtraction result; and multiplying the initial driving force with the subtraction result to obtain the target driving force.

14. The computer apparatus of claim 10, wherein the processing the target driving force and the floating frame to obtain the updated floating frame comprises:

performing regularization on the target driving force to determine a deformation field update amount for the floating frame;

updating an initial deformation field of the floating frame with the deformation field update amount to obtain the updated deformation field; and resampling, based on the updated deformation field, pixel values of pixels in the floating frame to obtain the updated floating frame.

15. The computer apparatus of claim 10, wherein the performing the motion correction on the background region in the updated floating frame comprises: performing one or more iterative operations, each iterative operation comprising:

determining the updated floating frame as a current floating frame;

performing, based on the reference frame and the mask, image registration on the background region in the current floating frame to obtain the motion corrected image of the current floating frame; and updating, based on the motion corrected image of the current floating frame, the current floating frame.

16. The computer apparatus of claim 15, wherein a convergence condition of the iterative operation is that a number of iterations reaches a preset iteration number threshold or a precision of the cross-correlation parameter reaches a preset precision.

17. The computer apparatus of claim 10, wherein the method further comprises performing motion analysis on a target region in the motion corrected image.

18. A non-transitory computer readable storage medium on which a computer program is stored, wherein the computer program, when executed by a computer, a method for medical image processing is implemented, the method comprising:

acquiring a plurality of frames of medical image data including a reference frame and at least one floating frame, each of the reference frame and at least one floating frame including a target region for a target organ, and a background region for other organs around the target organ;

performing image segmentation on the reference frame to obtain a mask for a target region in the reference frame; and performing, based on the reference frame and the mask, motion correction on the floating frame to obtain a motion corrected image corresponding to the floating frame, wherein the performing, based on the reference frame and the mask, the motion correction on the floating frame comprises:

determining, based on the reference frame and the floating frame, an initial driving force, the initial driving force representing an amount of a deformation of the target organ and the other organs in the floating frame with respect to the reference frame;

determining, based on the initial driving force and the mask, a target driving force;

processing the target driving force and the floating frame to obtain an updated floating frame; and performing motion correction on the background region in the updated floating frame; and wherein the motion corrected image is an image in which the motion correction has been performed on the background region in the updated floating frame but the motion correction has not been performed on the target region in the updated floating frame.

* * * * *